United States Patent [19]

Mullins et al.

[11] Patent Number: 4,912,232

[45] Date of Patent: Mar. 27, 1990

[54] PREPARATION OF N-HYDROCARBYLCARBONYL-5-(1-HYDROCARBYLCARBONYLOXY)HYDROCARBYL-PYRROLIDIN-2-ONE

[75] Inventors: Michael J. Mullins; Edmund P. Woo, both of Midland, Mich.

[73] Assignee: Dow Chemical Company, Midland, Mich.

[21] Appl. No.: 81,415

[22] Filed: Aug. 4, 1987

Related U.S. Application Data

[63] Continuation-in-part of Ser. No. 542,295, Oct. 14, 1983, abandoned.

[51] Int. Cl.$^4$ ............................................. C07D 207/12
[52] U.S. Cl. ................................... 548/539; 548/540; 562/553
[58] Field of Search ................................ 548/539, 540

[56] References Cited

U.S. PATENT DOCUMENTS 4,178,463 12/1979 Gittos et al. .................... 562/574
4,235,778 11/1980 Gittos et al. .................... 562/574 X
4,254,284 3/1981 Gittos et al. .................... 562/574

OTHER PUBLICATIONS

C.A. 51, 774, (1957), Hardegger et al.
Kolocouris, *Bull. Soc. Chim. France,* 3, 1053 (1973).
DePuy, Chem. Rev. 431 (1960).
Barco et al., *Farmaco,* 25, 669 (1970).

*Primary Examiner*—Joseph Paul Brust

[57] ABSTRACT

The invention is a process for the preparation of a N-hydrocarbylcarbonyl-5-(1-hydrocarbylcarbonyloxy)-hydrocarbylpyrrolidin-2-one which comprises contacting in an inert nonpolar organic solvent a hydrocarbyloxycarbonylpyrrolidin-2-one with
(a) an agent which forms a nitrogen-metal or nitrogen-metalloid bond;
(b) a reducing agent;
(c) an alkylating agent; and
(d) an acylating agent;
under conditions such that a N-hydrocarbylcarbonyl-5-(1-hydrocarbylcarbonyloxy)hydrocarbylpyrrolidin-2-one is prepared.

25 Claims, No Drawings

PREPARATION OF N-HYDROCARBYLCARBONYL-5-(1-HYDROCARBYLCARBONYLOXY)HYDROCARBYL-PYRROLIDIN-2-ONE

CROSS-REFERENCE TO RELATED APPLICATION

This application is a continuation-in-part application of application Ser. No. 542,295 filed on Oct. 14, 1983 now abandoned.

BACKGROUND OF THE INVENTION

This invention relates to the preparation of N-hydrocarbylcarbonyl-5-(1-hydrocarbylcarbonyloxy)-hydrocarbylpyrrolidin-2-one and to a process for the preparation of the S-enantiomer of this compound.

The N-hydrocarbylcarbonyl-5-(1-hydrocarbylcarbonyloxy)hydrocarbylpyrrolidin-2-ones are useful as intermediates in the preparation of 5-(1,2-ethylenically unsaturated hydrocarbyl)pyrrolidin-2-ones. The 5-(1,2-ethylenically unsaturated hydrocarbyl)pyrrolidin-2-ones are useful in the preparation of 4-amino-5-alkenoic acids which are known to have biological activity. In particular, 4-amino-5-alkenoic acids are known as irreversible inhibitors of γ-aminobutyric acid transaminose rendering the compounds useful in the treatment of disorders of the central nervous system function. It is the S-enantiomer of such compounds which show such activity.

The present processes for the preparation of 5-(1,2-ethylenically unsaturated hydrocarbyl)pyrrolidin-2-ones and the 4-amino-5-alkenoic acids involve complicated synthesis schemes and expensive reagents.

What is needed is a process in which the optical activity of the intermediates useful in the preparation of 5-(1,2-ethylenically unsaturated hydrocarbyl)pyrrolidin-2-one and 4-amino-5-alkenoic acids is retained. What is further needed is a process for the preparation of intermediates useful in the preparation of such compounds which uses relatively inexpensive reagents and involves relatively straightforward synthesis schemes.

SUMMARY OF THE INVENTION

The invention is a process for the preparation of a N-hydrocarbylcarbonyl-5-(1-hydrocarbylcarbonyloxy)hydrocarbylpyrrolidin-2-one which comprises contacting in an inert nonpolar organic solvent a 5-hydrocarbyloxycarbonylpyrrolidin-2-one with (a) an agent which forms a nitrogen-metal or nitrogen-metalloid bond;
(b) a reducing agent;
(c) an alkylating agent; and
(d) an acylating agent;

under conditions such that a N-hydrocarbylcarbonyl-5-(1-hydrocarbylcarbonyloxy)hydrocarbylpyrrolidin-2-one is prepared.

The N-hydrocarbylcarbonyl-5-(1-hydrocarbylcarbonyloxy)hydrocarbyl pyrrolidin-2-ones produced by the process of this invention are generally useful as extraction solvents and as solvents for the manufacture of polymers. The ethylenically unsaturated species of the aforementioned pyrrolidinones are also useful as monomers in the preparation of polymers.

Another aspect of this invention is a process for the preparation of the S-enantiomer of N-hydrocarbylcarbonyl-5-(1-hydrocarbylcarbonyloxy)hydrocarbylpyrrolidin-2-one. Specifically, where the starting compound in the described process is an optically active isomer, the product will retain that optical activity. Several of these S-enantiomers are biologically active and are useful as intermediates in the manufacture of 4-amino-5-alkenoic acids which are known as irreversible inhibitors of aminobutyric acid transaminose rendering the compounds useful in the treatment of disorders of the central nervous system function.

The process of this invention involves a relatively straightforward synthesis of N-hydrocarbylcarbonyl-5-(1-hydrocarbylcarbonyloxy)hydrocarbylpyrrolidin-2-ones wherein relatively inexpensive reagents are used.

DETAILED DESCRIPTION OF THE INVENTION

The N-hydrocarbylcarbonyl-5-(1-hydrocarbylcarbonyloxy)hydrocarbylpyrrolidin-2-ones (hereinafter hydrocarbylcarbonyl-substituted pyrrolidin-2-ones) prepared include those corresponding to the formula

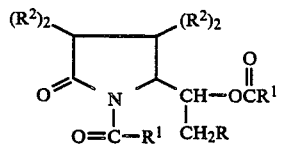

wherein

R is separately in each occurrence hydrogen, $C_{1-}$ aliphatic and $C_{7-20}$ alkaryl, wherein the $C_{1-20}$ aliphatic or $C_{7-20}$ alkaryl may optionally be substituted with a halo, thioalkyl, tert-amino, alkoxy, aryloxy or aralkoxy group;

$R^1$ is $C_{1-20}$ hydrocarbyl, preferably $C_{1-10}$ alkyl; and $R^2$ is separately in each occurrence hydrogen, a $C_{1-20}$ hydrocarbyl group or a $C_{1-20}$ hydrocarbyl group substituted with one or more of the following: a halo, thioalkyl, tert-amino, alkoxy, aryloxy, or aralkoxy group, preferably hydrogen or $C_{1-10}$ alkyl.

The 5-hydrocarbyloxycarbonylpyrrolidin-2-ones which are useful as starting reagents include those which correspond to the formula

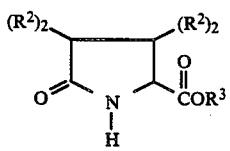

wherein $R^1$ and $R^2$ are as defined hereinbefore, and $R^3$ is hydrogen, a $C_{1-20}$ hydrocarbyl group, preferably alkyl, or a $C_{1-20}$ hydrocarbyl group substituted with one or more of the following: a halo, thioalkyl, tert-amino, alkoxy, aryloxy or aralkoxy group, preferably alkoxy.

These starting materials are readily prepared by first converting a 2-aminoalkane-1,5-dicarboxylic acid to a diester by any one of several known methods for esterifying carboxylic acids and then subjecting the diester to a cyclization reaction. One such method involves contacting the aminodicarboxylic acid with thionyl chloride and an alcohol corresponding to $R^3OH$ wherein $R^3$ is as defined hereinbefore. Thereafter the diester can be cyclized to the desired pyrrolidone by pyrolysis at a temperature of between about 150° C. and 200° C. It is preferred to carry out the pyrolysis under reduced pressure so that the pyrrolidinone continuously distills from the reaction mixture. For example, the cyclization reaction of L-glutamic acid or a substituted glutamic acid in the presence of thionyl chloride and strong base in an alcohol can be carried out as described in Silverman et al., *J. Org. Chem. Soc.*, 45, p 815-818 (1980). For the substituted glutamic acid, it is understood that the substituents represented by $R^2$ as defined hereinbefore are suitably those which do not interfere with the cyclization reaction, preferably hydrogen or alkyl having one to ten carbons.

In the preparation of the hydrocarbylcarbonyl-substituted pyrrolidin-2-ones by the process of this invention, the major by-products formed are N-hydrocarbylcarbonyl-5-(hydrocarbylcarbonyloxy)methylpyrrolidin-2-one and N-hydrocarbylcarbonyl-5-hydrocarbyloxycarbonylpyrrolidin-2-one. These by-products include those compounds which correspond to the following formulas

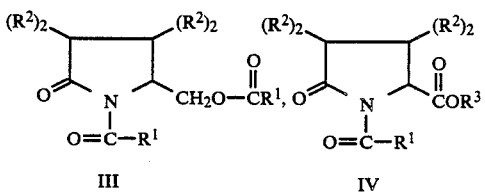

In the above formulas, R is preferably $C_{1-10}$ aliphatic, more preferably $C_{1-10}$ alkyl, even more preferably $C_{1-3}$ alkyl and most preferably methyl. $R^1$ is preferably $C_{1-10}$ aliphatic, more preferably $C_{1-10}$ alkyl, even more preferably $C_{1-3}$ alkyl and most preferably methyl. $R^2$ is preferably hydrogen or $C_{1-10}$ aliphatic, more preferably hydrogen or $C_{1-3}$ alkyl and most preferably hydrogen. $R^3$ is preferably $C_{1-10}$ aliphatic, more preferably $C_{1-10}$ alkyl, even more preferably $C_{1-3}$ alkyl and most preferably methyl.

Examples of N-hydrocarbylcarbonyl-5-(1-hydrocarbylcarbonyloxy)hydrocarbylpyrrolidin-2-ones include N-methylcarbonyl-5-(1-methylcarbonyloxy)ethylpyrrolidin-2-one; N-methylcarbonyl-5-(1-methylcarbonyloxy)propylpyrrolidin-2-one; N-methylcarbonyl-5-(1-methylcarbonyloxy)butylpyrrolidin-2-one; N-ethylcarbonyl-5-(1-ethylcarbonyloxy)ethylpyrrolidin-2-one; N-ethylcarbonyl-5-(1-ethylcarbonyloxy)propylpyrrolidin-2-one; N-ethylcarbonyl-5-(1-ethylcarbonyloxy)butylpyrrolidin-2-one; N-propylcarbonyl-5-(1-propylcarbonyloxy)ethylpyrrolidin-2-one; N-propylcarbonyl-5-(1-propylcarbonyloxy)propylpyrrolidin-2-one; N-propylcarbonyl-5-(1-propylcarbonyloxy)butylpyrrolidin-2-one; N-methylcarbonyl-3-methyl-5-(1-methylcarbonyloxy)ethylpyrrolidin-2-one; and N-methylcarbonyl-4-methyl-5-(1-methylcarbonyloxy)ethylpyrrolidin-2-one.

Examples of 5-hydrocarbyloxycarbonylpyrrolidin-2-ones include 5-methoxycarbonylpyrrolidin-2-one; 5-ethoxycarbonylpyrrolidin-2-one; 5-propoxycarbonylpyrrolidin-2-one; 3-methyl-5-methoxycarbonylpyrrolidin-2-one; 3-methyl-5-ethoxycarbonylpyrrolidin-2-one; 3-methyl-5-propoxycarbonylpyrrolidin-2-one; 4-methyl-5-methoxycarbonylpyrrolidin-2-one; 4-methyl-5-ethoxycarbonylpyrrolidin-2-one; and 4-methyl-5-propoxycarbonylpyrrolidin-2-one.

Hydrocarbyl means herein an organic radical containing carbon and hydrogen atoms. The term hydrocarbyl includes the following organic radicals: alkyl, alkenyl, alkynyl, cycloalkyl, cycloalkenyl, aryl, aliphatic and cycloaliphatic aralkyl and alkaryl. Aliphatic refers herein to straight- and branched-, and saturated and unsaturated, hydrocarbon chains, that is, alkyl, alkenyl or alkynyl. Cycloaliphatic refers herein to saturated and unsaturated cyclic hydrocarbons, that is, cycloalkenyl and cycloalkyl. The term aryl refers herein to biaryl, biphenylyl, phenyl, naphthyl, phenanthranyl, anthranyl and two aryl groups bridged by an alkylene group. Alkaryl refers herein to an alkyl-, alkenyl- or alkynyl-substituted aryl substituent wherein aryl is as defined hereinbefore. Aralkyl means herein an alkyl, alkenyl or alkynyl group substituted with an aryl group, wherein aryl is as defined hereinbefore. $C_{1-20}$ alkyl includes straight- and branched-chain methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl groups. $C_{1-5}$ alkyl includes methyl, ethyl, propyl, butyl and pentyl.

Cycloalkyl refers to alkyl groups containing one, two, three or more cyclic rings. Cycloalkenyl refers to mono-, di- and polycyclic groups containing one or more double bonds. Cycloalkenyl also refers to cycloalkenyl groups wherein two or more double bonds are present.

Hydrocarbylcarbonyloxy refers to a substituent in which a hydrocarbyl moiety is bonded to a carbonyl moiety which is further bonded to an oxygen atom and includes substituents which correspond to the formula

wherein $R^1$ is a hydrocarbyl moiety.

Hydrocarbylcarbonyl refers herein to a substituent which is a hydrocarbyl moiety bonded to a carbonyl moiety and includes substituents which correspond to the formula

wherein $R^1$ is a hydrocarbyl moiety.

Hydrocarbyloxycarbonyl refers herein to a substituent in which a hydrocarbyl moiety is bonded to an oxygen atom which is further bonded to a carbonyl moiety and includes substituents which correspond to the formula

wherein $R^3$ is a hydrocarbyl moiety.

The agent which forms a nitrogen-metal or nitrogen-metalloid bond is generally either an alkylating agent or a reducing agent. Alkylating agents are preferred. Agents which form a nitrogen-metal or nitrogen-metalloid bond include those compounds which correspond to the formula

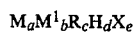

wherein
M and $M^1$ are separately in each occurrence a metal or metalloid;
R is a hydrocarbyl group;

X is an oxyhydrocarbyl group or a halogen; and a, b, c, d and e are separately in each occurrence an integer of from 0 to 4 inclusive;

with the proviso that the sum of a and b is 1 or greater, with the further proviso that a, b, c, d and e are such that the sum of the valences of M, M¹, R, H and X is zero.

Examples of agents which form nitrogen-metal or nitrogen-metalloid bonds include those compounds useful as alkylating agents and reducing agents named hereinafter.

The reducing agents useful in this invention are generally hydride reducing agents. Formula V describes compounds which are useful as reducing agents, wherein d is an integer of 1, 2, 3 or 4. Specifically, reducing agents include those which correspond to the formula $$M_a M^1_b R_c H_d X_e \qquad \text{V}$$

wherein M, M¹, R, X, a, b and e are as described hereinbefore; c is an integer of 0 to 3 inclusive; and d is an integer of from 1 to 4 inclusive.

In Formula V, a is preferably 0, 1 or 2 and more preferably 0 or 1. Preferably, b is 0, 1 or 2, more preferably 0 or 1. Preferably, c is 1 or 2 and most preferably 2. Preferably, d is 1 or 2. Preferably, e is 0, 1, 2 or 3 and most preferably 0.

Reducing agents useful in this invention include aluminum hydrides, boron hydrides, alkyl aluminum hydrides, alkali or alkaline earth metal aluminum hydrides, alkali or alkaline earth metal hydrides, alkali or alkaline earth metal borohydrides, aluminum alkoxy hydrides, alkali or alkaline earth metal alkoxy hydrides and alkali, alkaline earth metal alkyl hydrides or hexamethylbisilazene.

Preferred reducing agents include alkyl aluminum hydrides or alkali or alkaline earth metal alkyl aluminum hydrides. Most preferred are the alkyl aluminum hydrides.

Specific compounds useful as reducing agents include aluminum hydride, lithium hydride, sodium hydride, potassium hydride, lithium aluminum hydride, sodium borohydride, lithium borohydride, potassium borohydride, diisobutyl aluminum hydride, diisopropyl aluminum hydride, sodium bis(2-ethoxy-(2-ethoxy))-aluminum hydride, aluminum di-tert-butoxy hydride, and lithium aluminum tri-tert-butoxy hydride.

Alkylating agents useful in this invention include those described by formula VA wherein b and d are 0. Alkylating agents include those which correspond to the formula $$M_a R_c X_e \qquad \text{VA}$$

wherein M, R, X, a, c and e are as defined hereinbefore.

In formula VA, a is preferably 1 or 2 and most preferably 1; c is preferably 1, 2, 3 or 4 and most preferably 1, 2 or 3; and e is preferably 0, 1, 2 or 3 and most preferably 0 or 1.

Examples of alkylating agents include alkyl aluminums, alkyl aluminum halides, alkyl magnesium halides, dialkyl magnesiums, alkyl lithiums, alkyl sodiums and alkyl potassiums. Preferred alkylating agents include alkyl aluminums, alkyl lithiums and alkyl magnesium halides. Most preferred alkylating agents include trimethyl aluminum, methyl lithium, methyl magnesium bromide and methyl magnesium chloride.

In formulas V and VA, M and M¹ are preferably an alkali metal, an alkaline earth metal, aluminum, silicon, boron or zinc; more preferably lithium, sodium, magnesium or aluminum; and most preferably lithium or aluminum. R is preferably $C_{1-10}$ aliphatic, more preferably $C_{1-10}$ alkyl, even more preferably $C_{1-3}$ alkyl and most preferably methyl. X is preferably $C_{1-10}$ hydrocarbyloxy, or a halogen; more preferably $C_{1-4}$ alkoxy, chlorine or bromine; and most preferably chlorine or methoxy.

Acylating agents useful in this invention include anhydrides and acyl halides. Anhydrides useful in this invention include those corresponding to the formula $$\underset{R^1COCR^1}{\overset{\text{O O}}{\underset{\|\ \|}{}}} \qquad \text{VI}$$

and acyl halides useful in this invention include those corresponding to the formula $$\underset{R^1CY}{\overset{\text{O}}{\underset{\|}{}}} \qquad \text{VII}$$

wherein R¹ is as defined hereinbefore and Y is bromine, chlorine or iodine. Y is preferably bromine or chlorine, most preferably chlorine.

The reagents can be contacted with the 5-hydrocarbyloxycarbonylpyrrolidin-2-one in various sequences. In particular, all of the reagents can be contacted with the 5-hydrocarbyloxycarbonylpyrrolidin-2-one simultaneously. Alternatively, the 5-hydrocarbyloxycarbonylpyrrolidin-2-one can first be contacted with the compound which forms a nitrogen-metal or nitrogenmetalloid bond, thereafter the reaction product can be contacted with a reducing agent, thereafter the second reaction product can be contacted with the alkylating agent, and finally the third reaction product can be contacted with an acylating agent. In another embodiment, the 5-hydrocarbyloxycarbonylpyrrolidin-2-one first can be contacted with the compound which forms a nitrogen-metal or nitrogen-metalloid bond and an alkylating agent, thereafter the first reaction product is contacted with a reducing agent, and thereafter the second reaction product is contacted with an acylating agent. In this embodiment, it is preferable that the compound which forms a nitrogen-metal or nitrogen-metalloid bond be an alkylating agent. The sequential contacting is preferred over the simultaneous contacting because in the simultaneous contacting more by-product formation occurs.

It is believed that the compound which forms a nitrogen-metal or nitrogen-metalloid bond reacts to replace the hydrogen on the nitrogen in the pyrrolidin-2-one ring, by forming a nitrogen-metal or nitrogen-metalloid bond. It is believed that the formation of such bonds protects the pyrrolidin-2-one ring at the nitrogen or the carbonyl group bonded to the nitrogen from attack by the alkylating or reducing agents throughout the process of this invention.

It is believed that the reducing agent reduces the carbonyl moiety of the hydrocarbyloxycarbonyl substituent. It is further believed that the alkylating agent adds an alkyl group to the reduced carbonyl moiety. It is also believed that the acylating agent functions to replace the residue of the compound which forms a nitrogen-metal or nitrogen-metalloid bond on the nitrogen with a hydrocarbylcarbonyl moiety and to insert a hydrocarbylcarbonyl moiety on the reduced carbonyl carbon.

The preparation of the hydrocarbylcarbonyloxy-substituted pyrrolidin-2-ones is done in an inert nonpolar organic solvent. Preferred nonpolar organic solvents include chlorinated aromatic hydrocarbons, aromatic hydrocarbons and chlorinated aliphatic hydrocarbons. Aromatic hydrocarbons are more preferred.

The amount of solvent used is not critical, provided a sufficient amount is used to dissolve the reactants, and that the amount is not so large as to render the heat transfer uneconomical.

The reagents can be added to the solution of the 5-hydrocarbyloxycarbonylpyrrolidin-2-one using standard methods well-known in the art. One advantageous manner involves adding the reagents directly to the solution. Another advantageous manner involves dissolving the reagent in one of the solvents described hereinbefore and adding the solution to the reaction solution.

The 5-hydrocarbyloxypyrrolidin-2-one is contacted with an agent which forms a nitrogen-metal or nitrogen-metalloid bond at a temperature at which a nitrogen-metal or nitrogen-metalloid bond is formed. Preferable temperatures are between about $-78°$ C. and $50°$ C. Reaction temperatures are more preferably between about $-30°$ C. and $35°$ C., most preferably between about $-30°$ C. and $-10°$ C.

Contacting with the reducing agent is done at any temperature at which reduction of the carbonyl occurs. Temperatures are preferably between about $-78°$ C. and $50°$ C., more preferably between about $-78°$ C. and $-20°$ C. with between about $-78°$ C. and $-30°$ C. being most preferred.

Contacting with the alkylating agent is done at any temperature at which alkylation occurs. Such a temperature is preferably between about $-78°$ C. and $50°$ C., more preferably between about $-78°$ C. and $35°$ C. and most preferably between about $-30°$ C. and $25°$ C.

Contacting with the acylating agent is done at any temperature at which acylation occurs. Such a temperature is preferably between about $-78°$ C. and $50°$ C., more preferably between about $-30°$ C. and $25°$ C. and most preferably between about $-30°$ C. and $-10°$ C.

The above-described reactants react with 5-hydrocarbyloxycarbonylpyrrolidin-2-ones in a stoichiometric manner, thus although any amount of such reactants is suitable for this reaction, generally about a stoichiometric amount is preferred. It is preferable to use between 1.05 and 0.95 equivalents of a compound which forms a nitrogen-metal of nitrogen-metalloid bond per equivalent of the 5-hydrocarbyloxycarbonylpyrrolidin-2-one.

The amount of reducing agent used is preferably between about 10.0 and 0.1 equivalents per equivalent of 5-hydrocarbyloxycarbonylpyrrolidin-2-one, with between about 0.5 and 1.5 equivalents being preferred and 0.8 to 1.0 being most preferred. A small deficiency of reducing agent is preferred so as to avoid the formation of by-products.

Preferably, between 0.95 and 1.05 equivalents of an alkylating agent is used per equivalent of 5-hydrocarbyloxycarbonylpyrrolidin-2-one. Preferably, between 1.95 and 2.05 equivalents of an acylating agent is used. Wherein an anhydride is used, each mole of anhydride contains one equivalent. An acyl halide only contains one equivalent per mole.

This reaction generally takes place at atmospheric pressure although both superatmospheric and subatmospheric pressures can be used.

In the embodiment wherein the various reagents are added in a sequential manner, the time between the addition of each reagent is not critical, thus any reasonable period of time between such additions is suitable. In one preferred embodiment, the lower limit on time between additions is such that each reagent is added immediately after the addition of the previously added reagent is completed, with the upper limit on such time being about 15 minutes.

One significant advantage of this invention is that the optical activity of a 5-hydrocarbyloxycarbonylpyrrolidin-2-one is retained throughout the process, that is, no racemization occurs during this process. In particular, the 5 carbon is optically active in 5-hydrocarbyloxycarbonylpyrrolidin-2-ones and the hydrocarbonyl-substituted pyrrolidin-2-ones. Thus, in order to prepare the S-enantiomer of the hydrocarbonyl-substituted pyrrolidin-2-ones, the starting reagent needs to be the S-enantiomer of the 5-hydrocarbyloxycarbonylpyrrolidin-2-ones. In one aspect, this invention is a process for the preparation of the S-enantiomer of N-hydrocarbylcarbonyl-5-(1-hydrocarbylcarbonyloxy)hydrocarbylpyrrolidin-2-one which comprises contacting the S-enantiomer of a 5-hydrocarbyloxycarbonylpyrrolidin-2-one with the reagents described hereinbefore in the manner described hereinbefore.

The hydrocarbylcarbonyl-substituted pyrrolidin-2-ones prepared by this invention can be pyrolyzed at a temperature such that a 5-(1,2-ethylenically substituted hydrocarbyl)pyrrolidin-2-one is prepared. Preferably, temperatures are between about $200°$ C. and $600°$ C. More preferable temperatures are between about $500°$ C. and $550°$ C.

The pyrolysis may take place in the presence of a support with structural integrity which is capable of heat transfer. Any support which is inert, has structural integrity and provides heat transfer can be used in this invention. Examples of suitable supports include aluminas, silica gels, clays, zeolites, diatomaceous earth, glass beads, Carborundum ®, steel helices, activated carbon silicalite and the like.

Generally, the N-hydrocarbylcarbonyl-5-(1-hydrocarbylcarbonyloxy)hydrocarbylpyrrolidin-2-ones are pyrolyzed in neat form, i.e., in the absence of a solvent.

The pyrolysis can take place in any apparatus which is capable of exposing the hydrocarbylcarbonyl-substituted pyrrolidin-2-one to pyrolysis temperatures. In one preferred embodiment a hot tube is used. In this embodiment the starting reagent is dropped through a hot tube which is at pyrolysis temperatures.

The hydrocarbylcarbonyl-substituted pyrrolidin-2-ones are exposed to pyrolysis conditions for a period of time sufficient for the reagent to reach the appropriate thermal state at which cracking occurs. As the temperature is increased, the time needed for the starting reagent to reach such thermal state is shortened. Preferred pyrolysis times are between about 0.1 and 100 seconds, more preferably between about 0.5 and 10 seconds and most preferably between about 1 and 3 seconds.

Optionally, the hydrocarbylcarbonyl-substituted pyrrolidin-2-one can be pyrolyzed in the presence of a dehydration catalyst. Suitable dehydration catalysts include metal oxides.

Generally, this process is run at atmospheric pressure, although any pressure at which the pyrolysis occurs is suitable, including subatmospheric and superatmospheric pressures. This process is preferably done in the vapor phase.

The major product of the pyrolysis is the 5-(1,2-ethylenically unsaturated hydrocarbyl)pyrrolidin-2-one, with a by-product being a N-hydrocarbylcarbonyl-5-(1,2-ethylenically unsaturated hydrocarbyl)pyrrolidin-2-one. The 5-(1,2-ethylenically unsaturated hydrocarbyl)pyrrolidin-2-one corresponds to the formula

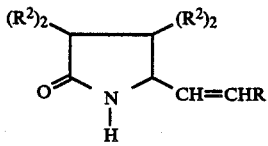

VIII and the N-hydrocarbylcarbonyl-5-(1,2-ethylenically unsaturated hydrocarbyl)pyrrolidin-2-ones correspond to the formula

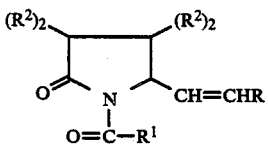

IX wherein R, $R^1$ and $R^2$ are as defined hereinbefore.

The 5-(1,2-ethylenically unsaturated hydrocarbyl)-pyrrolidin-2-ones can be contacted with a strong acid at temperatures of between about 60° C. to about 150° C. so as to hydrolyze the pyrrolidinones for about 2 to 24 hours. The temperature used is preferably between 100° C. and 150° C. Preferable strong acids include hydrochloric, hydrobromic, methanesulfonic, toluenesulfonic or trifluoroacetic. The hydrolyzed product is a 4-amino-5-alkenoic acid which corresponds to the formula

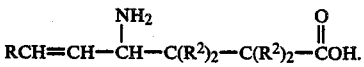

4-Amino-5-alkenoic acids are pharmacologically active compounds. In one preferred embodiment wherein a 5-vinylpyrrolidin-2-one is hydrolyzed, the product is 4-amino-5-hexenoic acid.

Hydrolysis of both the 5-(1,2-ethylenically unsaturated hydrocarbyl)pyrrolidin-2-one and the N-hydrocarbylcarbonyl-5-(1,2-ethylenically unsaturated hydrocarbyl)pyrrolidin-2-one results in the preparation of 4-amino-5-alkenoic acids. It is preferable that the N-hydrocarbylcarbonyl-5-(1,2-ethylenically unsaturated hydrocarbyl)pyrrolidin-2-one be converted to the 5-(1,2-ethylenically unsaturated hydrocarbyl)pyrrolidin-2-one before hydrolysis to simplify purification of the hydrolysis product. This conversion is achieved by treatment of the N-hydrocarbylcarbonyl-5-(1,2-ethylenically unsaturated hydrocarbyl)pyrrolidin-2-one with an alkanol, preferably methanol, in the presence of a small amount of acid.

One aspect of this invention is a process for the preparation of a 4-amino-5-alkenoic acid, wherein the process comprises (1) contacting a 2-aminoalkane-1,5-dicarboxylic acid with an alcohol in the presence of thionyl chloride under conditions such that a 1,5-diester of 2-aminoalkane is prepared;

(2) pyrolyzing the 1,5-diester of 2-aminoalkane at a temperature of between 150° C. and 200° C. under conditions such that a 5-hydrocarbyloxycarbonylpyrrolidin-2-one is prepared;

(3) contacting in an inert nonpolar organic solvent the 5-hydrocarbyloxycarbonylpyrrolidin-2-one with
  (a) an agent which forms a nitrogen-metal or nitrogen-metalloid bond;
  (b) a reducing agent;
  (c) an alkylating agent; and
  (d) an acylating agent;
under conditions such that a N-hydrocarbylcarbonyl-5-(1-hydrocarbylcarbonyloxy)hydrocarbylpyrrolidin-2-one is prepared;

(4) pyrolyzing the N-hydrocarbylcarbonyl-5-(1-hydrocarbylcarbonyloxy)hydrocarbylpyrrolidin-2-one under conditions such that a 5-(1,2-ethylenically unsaturated hydrocarbyl)pyrrolidin-2-one is prepared; and (5) contacting the 5-(1,2-ethylenically unsaturated hydrocarbyl)pyrrolidin-2-one with a strong acid at a temperature of between about 60° C. and about 150° C. for between 2 and 24 hours under conditions such that a 4-amino-5-alkenoic acid is prepared.

Another aspect of this invention is the preparation of the S-enantiomer of the 4-amino-5-alkenoic acid. This is achieved by using the S-enantiomer of the 2-aminoalkane-1,5-dicarboxylic acid as the initial starting reagent. The optical activity of the 2 carbon of the 2-aminoalkane-1,5-dicarboxylic acid is retained throughout the entire synthesis.

In one preferred embodiment, 4-amino-5-hexenoic acid is prepared by the synthesis scheme disclosed herein, wherein the initial starting reagent is glutamic acid (2-aminopentane-1,5-dicarboxylic acid). In a more preferred embodiment, the S-enantiomer of 4-amino-5-hexenoic acid is prepared wherein the S-enantiomer of glutamic acid is the initial starting reagent, L-glutamic acid.

The process for the preparation of 4-amino-5-hexenoic acid comprises (1) contacting a glutamic acid (2-aminopentane-1,5-dicarboxylic acid) with an alcohol in the presence of thionyl chloride under conditions such that a 1,5-diester of 2-aminopentane is prepared;

(2) pyrolyzing the 1,5-diester of 2-aminopentane at a temperature of between 150° C. and 200° C. under conditions such that a 5-hydrocarbyloxycarbonylpyrrolidin-2-one is prepared;

(3) contacting in an inert polar solvent the 5-hydrocarbyloxycarbonylpyrrolidin-2-one with
  (a) an agent which forms a nitrogen-metal or nitrogen-metalloid bond;
  (b) a reducing agent;
  (c) a methylating agent; and
  (d) an acylating agent;
under conditions such that a N-hydrocarbylcarbonyl-5-(1-hydrocarbylcarbonyloxy)ethylpyrrolidin-2-one is prepared;

(4) pyrolyzing the N-hydrocarbylcarbonyl-5-(1-hydrocarbylcarbonyloxy)ethylpyrrolidin-2-one under conditions such that a 5-vinylpyrrolidin-2-one is prepared; and (5) contacting the 5-vinylpyrrolidin-2-one with a strong acid at a temperature of between about 60° C. and about 150° C. for between about 2 and 24 hours under conditions such that 4-amino-5-hexenoic acid is prepared.

SPECIFIC EMBODIMENTS

The following examples are included for illustrative purposes and do not limit the scope of the invention or the claims. All parts and percentages are by weight unless otherwise specified.

EXAMPLE 1

Preparation of N-acetyl-5-(1-acetoxyethyl)pyrrolidin-2-one

A 100-ml flask is charged with 1.857 g (13.11 mmole) of 5-methoxycarbonylpyrrolidin-2-one, 10 ml of $CH_2Cl_2$ and cooled to 0° C. in a nitrogen atmosphere. A solution of trimethyl aluminum (8.0 ml, 2M in toluene) is added over a 5-minute period. This reaction is noticeably exothermic. The colorless solution is immediately cooled to −78° C. in acetone-dry ice and treated with $Bu_2AlH$ (7.0 ml, 1.46M in toluene) over a 10-minute period. Trimethyl aluminum (8.0 ml, 2M in toluene) is then added immediately over a 5-minute period. After 15 minutes at −78° C., the solution is allowed to warm to 20° C. (this requires about 20 minutes) and treated with 25 ml acetic anhydride. The resultant pale yellow solution is poured slowly onto about 10 g ice. Although a great deal of gas is evolved in this latter quenching process, it is easily controllable. The white slurry is then treated with concentrated HCl until the aluminum salts dissolve. The layers are separated and the aqueous layer was washed 3 times with 10 ml methylene chloride. The combined organic layers are washed twice with 10 ml saturated NaCl solution, dried with $Na_2SO_4$, filtered and evaporated. After overnight evacuation to further remove volatile materials, 2.014 g of a viscous yellow oil results. Analysis by gas chromatography (6 foot packed FFAP column) and by $^{13}C$ nuclear magnetic resonance (NMR) indicates a 1.3 to 1 ratio of the N-acetyl-5-(1-acetoxyethyl)pyrrolidin-2-one (38 percent yield) to the undesired N-acetyl-5-(1-acetoxymethyl)-pyrrolidin-2-one.

EXAMPLE 2

Preparation of N-acetyl-5-(1-acetoxyethyl)pyrrolidin-2-one

A solution of methoxycarbonylpyrrolidin-2-one (10.0 g, 69.9 mmoles) in 80 ml of $CH_2Cl_2$ is cooled to −30° C. using an ethanol-water slush bath and treated with trimethyl aluminum (35 ml, 2M in toluene) over a 10-minute period. After a 15-minute wait, diisobutyl aluminum hydride (41.1 ml, 1.46M in toluene, 60.0 mmoles) is added over a 45-minute period. The internal temperature is maintained at −28° C. to −35° C. during this time. Trimethyl aluminum (35 ml, 2M in toluene) is then added immediately over a 10-minute period, maintaining the same temperature. After 40 minutes, 35 ml of acetic anhydride is added. The temperature is allowed to warm to 14° C. over 20 minutes, and the pale yellow reaction is then poured carefully onto about 150 g of ice with vigorous stirring. Concentrated aqueous HCl is then added to dissolve the aluminum salts during which the temperature is maintained at 0° C. The layers are separated and the aqueous phase washed 4 times with 30 ml of $CH_2Cl_2$. The combined organic layers are twice washed with concentrated NaCl, dried with $MgSO_4$, filtered, evaporated and evacuated for 1 hour to yield 11.48 g of a pale yellow oil. Analysis by gas chromatography and nuclear magnetic resonance indicates the presence of the desired N-acetyl-5-(1-acetoxyethyl)pyrrolidin-2-one, the N-acetyl-5-(1-acetoxymethyl)pyrrolidin-2-one and the N-acetyl-5-(methoxycarbonyl)pyrrolidin-2-one in about a 1 to 1 to 0.8 ratio, respectively.

EXAMPLE 3

Preparation of optically active N-acetyl-5-vinylpyrrolidin-2-one and 5-vinylpyrrolidin-2-one A 10.99-g sample of optically active N-acetyl-5-(1-acetoxyethyl)pyrrolidin-2-one (purity about 50 percent pure, N-acetyl-5-(1-acetoxymethyl)pyrrolidin-2-one, N-acetyl-5-(1-methoxycarbonyl)pyrrolidin-2-one and unknown impurity made up the remainder in approximately equal proportions) is introduced at the top of a 300-mm long by 12-mm inside diameter Vycor glass tube filled with quartz chips using a 2-ml per second nitrogen flow. The column is maintained at 530° C. to 545° C. during the 35 minutes used to drip in the acetates. The pyrolysate is condensed into a 100-ml round-bottom cooled with acetone-dry ice. The red, viscous oil is directly distilled at 0.7 mm Hg vacuum. The fraction distilling at 100° C. to 110° C. (4.346 g) is kept. Analysis by nuclear magnetic resonance and gas chromatography indicates that this material is about 55 percent by weight of the desired products, the optically active acetylated 5-vinylpyrrolidin-2-one and the related optically active deacetylated 5-vinylpyrrolidin-2-one in an approximately 2 to 1 ratio, respectively.

EXAMPLE 4

Preparation of 4(S)-amino-5-hexenoic acid

The distilled product from Example 3 minus 0.20 g (4.14 g net) is dissolved in 12 ml 6M aqueous HCl and heated to reflux. After 3 hours, gas chromatographic analysis indicates that none of the cyclized starting materials remains. Most of the excess acid is distilled off under vacuum at 40° C.–50° C. The pot is then heated to 100° C. for 10 minutes and 14 mm HG vacuum was applied. Ethanol (10 ml) is then added and partially distilled off at atmospheric pressure to further dehydrate the sample. The extremely viscous red-brown oil is then dissolved in 10 ml of isopropanol and the pH is adjusted to 7.14 using triethylamine. The tan solid which forms immediately ($Et_3NHCl$) is filtered off. The filtrate is then heated to boiling and isopropanol is then added until the solution becomes cloudy. Tan crystals (795 mg) of the 4(S)-amino-5-hexenoic acid form on standing overnight. The optical rotation of this sample is found to be identical to that of a sample of 4(S)-amino-5-hexenoic acid.

EXAMPLE 5

Removal of the acetate from N-acetyl-5-vinylpyrrolidin-2-one

A nuclear magnetic resonance tube containing a solution of 100 mg of the distilled pyrolysate from Example 3 in $CDCl_3$ is treated with 0.10 ml of MeOH and a very small crystal of toluene sulfonic acid. The sample is briefly heated to reflux and the nuclear magnetic resonance spectrum run immediately. The ratio of non-acetylated 5-vinylpyrrolidin-2-one to that of the acetylated 5-vinylpyrrolidin-2-one increases. This cleavage continues to occur at room temperature and is about 50 percent complete after two days at room temperature.

What is claimed is:

1. A process for the preparation of an N-substituted pyrrolidin-2-one which corresponds to the formula

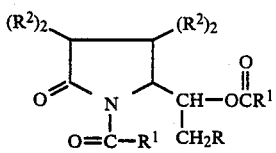

wherein
R is separately in each occurrence $C_{1-20}$ alkyl, $C_{7-20}$ alkaryl, substituted $C_{1-20}$ alkyl or substituted $C_{7-20}$ alkaryl wherein the substituent is halo, thioalkyl, tert-amino, alkoxy, aryloxy or aralkoxy;
$R^1$ is $C_{1-20}$ alkyl or aryl; and
$R^2$ and $R^3$ are separately in each occurrence hydrogen, a $C_{1-20}$ alkyl group or a $C_{1-20}$ alkyl group substituted with one or more of the following: halo, thioalkyl, tert-amino, alkoxy, aryloxy or aralkoxy which process comprises contacting in an inert nonpolar organic a pyrrolidin-2-one which corresponds to the formula

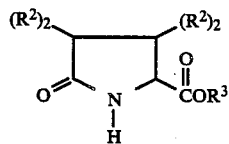

wherein $R^2$ and $R^3$ are as defined above with
(a) an agent which forms a nitrogen-metal or nitrogen-metalloid bond;
(b) a reducing agent;
(c) an alkylating agent; and
(d) an acylating agent;
under conditions such that the N-substituted pyrrolidin-2-one is prepared.

2. The process of claim 1 wherein the compound which forms a nitrogen-metal or nitrogen-metalloid bond corresponds to the formula $$M_aM^1_bR_cH_dX_e$$

wherein
M and $M^1$ are separately in each occurence an alkali metal, alkaline earth metal, aluminum, zinc, silicon or boron;
each R is independently a $C_{1-20}$ alkyl, $C_{7-20}$ alkaryl, substituted $C_{1-20}$ alkyl or substituted $C_{7-20}$ alkaryl wherein the substituent is halo, thioalkyl, tert-amino, alkoxy, aryloxy or aralkoxy group;
each X is independently $C_{1-10}$ oxyalkyl or halogen; and
a, b, c, d and e are separately in each occurrence an integer of from 0 to 4 inclusive;
with the proviso that the sum of a and b is 1 or greater and with the further proviso that a, b, c, d and e are such that the sum of the valences of M, $M^1$, R, H and X is zero.

3. The process of claim 2 wherein M and $M^1$ are separately in each occurrence lithium, sodium, magnesium, aluminum or boron; R is $C_{1-3}$ alkyl; and X is chlorine, bromine or $C_{1-3}$ alkoxy.

4. The process of claim 2 wherein M and $M^1$ are separately in each occurrence lithium or aluminum; R is methyl; and X is chlorine or methoxy.

5. The process of claim 1 wherein the reducing agent corresponds to the formula $$M_aM^1_bR_cH_dX_e$$

wherein
M and $M^1$ are separately in each occurrence an alkali metal, alkaline earth metal, aluminum, zinc, silicon or boron;
R is alkyl;
X is an oxyalkyl or a halogen;
a, b, c and e are separately in each occurrence an integer of from 0 to 4 inclusive; and
d is an integer of from 1 to 4;
with the proviso that the sum of a and b is equal to or greater than 1.

6. The process of claim 5 wherein R is $C_{1-10}$ alkyl; and X is $C_{1-10}$ alkoxy or halogen.

7. The process of claim 5 wherein a and b are 0, 1 or 2; c is 0, 1, 2 or 3; d is 1 to 2; and e is 0, 1, 2 or 3.

8. The process of claim 5 wherein the reducing agent is a hydride reducing agent.

9. The process of claim 8 wherein the reducing agent is aluminum hydride, boron hydride, an alkyl aluminum hydride, an alkali or alkaline earth metal hydride, an alkali or alkaline earth metal borohydride, or a hexamethyl bisilazene.

10. The process of claim 9 wherein the reducing agent is an alkyl aluminum hydride or an alkali or alkaline earth metal alkyl aluminum hydride.

11. The process of claim 5 wherein the alkylating agent corresponds to the formula $$M_aR_cX_e$$

wherein each M is independently an alkali metal, an alkaline earth metal, aluminum, zinc, silicon or boron; each R is independently alkyl; each X is a hydrocarbyloxy independently alkoxy or a halogen; a is an integer of 1 to 4; c is an integer of 0 to 4; and e is an integer of 0 to 4.

12. The process of claim 11 wherein R is $C_{1-10}$ alkyl; and X is $C_{1-10}$ alkoxy or a halogen.

13. The process of claim 11 wherein a is 1 or 2; c is 1, 2, 3 or 4; and e is 0, 1, 2 or 3.

14. The process of claim 5 wherein the alkylating agent is a trialkyl aluminum, an alkyl aluminum halide, an alkyl magnesium halide, a dialkyl magnesium or an alkyl lithium.

15. The process of claim 5 wherein the alkylating agent is a trialkyl aluminum.

16. The process of claim 2 wherein the acylating agent is an anhydride which corresponds to the formula

or an acyl halide which corresponds to the formula

wherein $R^1$ is a hydrocarbyl radical and X is chloride, bromine or iodine.

17. The process of claim 1 wherein the 5-alkyloxycarbonylpyrrolidin-2-one is first contacted with (a) an agent which forms a nitrogen-metal or nitrogen-metalloid bond; thereafter the reaction product is contacted with (b) a reducing agent; thereafter the second reaction product is contacted with (c) an alkylating agent; and thereafter the third reaction product is contacted with (d) an acyl chloride or anhydride.

18. The process of claim 2 wherein the 5-alkyloxycarbonylpyrrolidin-2-one is first contacted with (a) an agent which forms a nitrogen-metal or nitrogen-metalloid bond and (c) an alkylating agent simultaneously; thereafter the reaction product is contacted with (b) a reducing agent; and thereafter the reaction product is contacted with (d) an acyl halide or anhydride.

19. The process of claim 17 wherein the agent which forms a nitrogen-metal or nitrogen-metalloid bond is the same compound as the alkylating agent (c).

20. The process of claim 2 wherein the contacting with the alkylating agent occurs at a temperature of between about $-78°$ C. and $35°$ C.

21. The process of claim 16 wherein the contacting with the acyl chloride or anhydride occurs at a temperature of between about $-30°$ C. and $25°$ C.

22. The process of claim 2 wherein 5-methoxycarbonylpyrrolidin-2-one is contacted in an inert nonpolar organic solvent with trimethyl aluminum and acetic anhydride under conditions sufficient to form N-acetyl-5-(1-acetoxyethyl)-pyrrolidin-2-one.

23. The process of claim 8 wherein the reducing agent is an alkali metal aluminum hydride or an alkaline earth metal aluminum hydride.

24. The process of claim 8 wherein the reducing agent is an aluminum alkoxy hydride, an alkali metal alkoxy hydride or an alkaline earth metal alkoxy hydride.

25. The process of claim 8 wherein the reducing agent is an alkali metal alkyl hydride or an alkaline earth metal hydride.

* * * * *